United States Patent [19]

Berges

[11] 4,126,682

[45] Nov. 21, 1978

[54] 7-ACYL-3-(CARBOXYALKYL AND CARBAMOYLALKYL SUBSTITUTED OXADIAZOLYLTHIOMETHYL) CEPHALOSPORINS AND ANTIBACTERIAL COMPOSITIONS AND METHODS EMPLOYING THEM

[75] Inventor: David A. Berges, Wayne, Pa.

[73] Assignee: SmithKline Corporation, Philadelphia, Pa.

[21] Appl. No.: 779,202

[22] Filed: Mar. 18, 1977

Related U.S. Application Data

[62] Division of Ser. No. 682,948, May 3, 1976, Pat. No. 4,034,092.

[51] Int. Cl.$^2$ ............... C07D 501/50; A61K 31/545; C07D 501/56
[52] U.S. Cl. ............................ 424/246; 544/26; 544/27; 260/307 G
[58] Field of Search ............ 260/243 C; 424/246; 544/26, 27

[56] References Cited

U.S. PATENT DOCUMENTS

| | | | |
|---|---|---|---|
| 3,819,623 | 6/1974 | Takano et al. | 260/243 C |
| 3,828,037 | 8/1974 | De Marinis et al. | 260/243 C |
| 3,865,819 | 2/1975 | De Marinis et al. | 260/243 C |
| 3,883,520 | 5/1975 | De Marinis | 260/243 C |
| 4,012,379 | 3/1977 | Numata et al. | 260/243 C |
| 4,012,382 | 3/1977 | Bouzard et al. | 260/243 C |

FOREIGN PATENT DOCUMENTS 47-05550  2/1972  Japan.

*Primary Examiner*—Donald G. Daus
*Assistant Examiner*—Diana G. Rivers
*Attorney, Agent, or Firm*—Janice E. Williams; William H. Edgerton; Alan D. Lourie

[57] ABSTRACT

The compounds of this invention are cephalosporins having various acyl substituents at the 7-position and a carboxyalkyl or carbamoylalkyl substituted oxadiazolylthiomethyl group at the 3-position of the cephem nucleus and intermediates for the preparation thereof. The 7-acylated compounds have antibacterial activity.

11 Claims, No Drawings

7-ACYL-3-(CARBOXYALKYL AND CARBAMOYLALKYL SUBSTITUTED OXADIAZOLYLTHIOMETHYL) CEPHALOSPORINS AND ANTIBACTERIAL COMPOSITIONS AND METHODS EMPLOYING THEM

This is a divisional of application Ser. No. 682,948 filed May 3, 1976, now U.S. Pat. No. 4,034,092 issued July 5, 1977.

This invention relates to a new series of cephalosporin compounds which have antibacterial activity when administered parenterally and orally and to intermediates for the preparation thereof. In particular, the structures of the biologically active cephalosporin compounds of this invention are characterized by having a carboxyalkyl or carbamoylalkyl substituted oxadiazolylthiomethyl group at the 3-position of the cephem nucleus. Also, this invention extends to methods and compositions for treating certain bacterial infections using these new compounds as well as to certain chemical intermediates and methods for preparing the compounds described hereafter.

The compounds of this invention are represented by the following structural formula:

FORMULA I

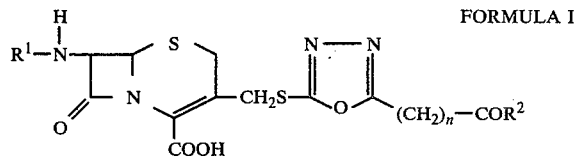

in which:

$R^1$ is an acyl group selected from the group consisting of:

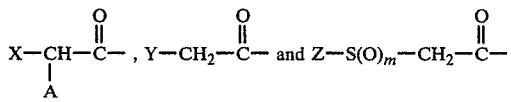

where:

X is thienyl; dihydrophenyl; phenyl or phenyl monosubstituted with hydroxy, hydroxymethyl, formamido, ureido or carboxymethylamino;

A is $NH_2$, OH, COOH or $SO_3H$; or formyloxy when X is phenyl;

Y is cyano, aminomethylphenyl, sydnone, pyridone, thienyl or tetrazolyl;

Z is methyl, trifluoromethyl, trifluoroethyl, pyridyl or cyanomethyl;

$m$ is 0 to 2;

$n$ is 1 to 5; and $R^2$ is hydroxy, amino, lower alkylamino or di(-lower)alkylamino, or a non-toxic pharmaceutically acceptable salt thereof.

As used herein, the term "lower alkyl" refers to groups containing from one to four carbon atoms.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such esters are included within the scope of this invention.

A particular group of compounds of this invention is represented by Formula I where $n$ is 1 and $R^2$ is hydroxy.

Another group of compounds of this invention is represented by Formula I where $n$ is 1, $R^2$ is hydroxy and $R^1$ is

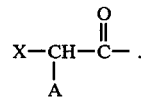

A more particular group of compounds is that represented by Formula I where $n$ is 1, $R^2$ is hydroxy, $R^1$ is

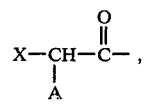

X is phenyl or hydroxyphenyl and A is $NH_2$ or OH.

Examples of some 7-acyl substituents ($R^1NH$—) of the compounds of Formula I are listed below:

α-hydroxyphenylacetamido
α-aminophenylacetamido
α-amino-4-hydroxyphenylacetamido
trifluoromethylthioacetamido
methylthioacetamido
2,2,2-trifluoroethylsulfinylacetamido
cyanoacetamido
α-carboxythienylacetamido
α-carboxyphenylacetamido
α-sulfophenylacetamido
methylsulfonylacetamido
cyanomethylthioacetamido
α-amino-4-carboxymethylaminophenylacetamido
2-aminomethylphenylacetamido
3-sydnoneacetamido
1-tetrazolylacetamido
2-thienylacetamido
2-pyridoneacetamido
4-pyridoneacetamido
4-pyridylthioacetamido.

An example of the compounds of this invention is the compound 7-D-mandelamido-3-(5-carboxymethyl-1,3,4-oxadiazol-2-ylthiomethyl)-3-cephem-4-carboxylic acid.

Cephalosporin derivatives having the 7-acyl substituents defined above are all documented in the prior art. Substitution by a substituted S-heterocyclicthiomethyl group (—$CH_2SHet$) where Het includes oxadiazolyl at the 3-position of the cephem nucleus is also known and is generically disclosed in Belgian Pat. No. 814,546 where the heterocyclic ring also may be substituted by, among others, carboxy; in Belgian Pat. Nos. 808,906 and 818,209 where the heterocyclic ring is substituted by, among others, carboxyalkyl; in U.S. Pat. No. 3,819,623, Netherlands Pat. No. 6916131, Belgian Pat. No. 827,600 and German Offenlegungschrift No. 2,445,071 where the heterocyclic ring is substituted by, inter alia, carboxy and carboxyalkyl; in U.S. Patent 3,883,520 where the heterocyclic ring is substituted by, among others, carboxy and carboxamido; in Belgian Pat. No. 823,861 where the heterocyclic ring is substituted by, inter alia, carboxy, carboxyalkyl, carbamoyl and carbamoylalkyl; and in Japanese Pat. No. 7205550 where the heterocyclic ring is substituted by —(CH$_2$)$_n$R$^3$ where $n$ is 0 to 3 and R$^3$ includes carboxy and N-alkoxyalkylcarbamoyl. No specific example of any cephalosporin containing a 3-oxadiazolylthiomethyl group substituted by carboxy, carboxyalkyl, carbamoyl or carbamoylalkyl, especially with the 7-acyl groups here disclosed, is believed to be known to the art.

The compounds of Formula I are preferably prepared by acylating 7-aminocephalosporanic acid (7-ACA) with an appropriate acylating agent, suitably protected as necessary, and then displacing the 3-acetoxy group with the desired substituted oxadiazole thiol of the formula:

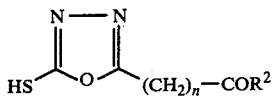
FORMULA II in which:
$n$ is 1 to 5; and
R$^2$ is hydroxy, amino, lower alkylamino or di(lower)alkylamino,
with subsequent removal of the protective group(s). When certain acylating agents are used, for example activated and protected derivatives of mandelic acid, it is preferable to remove the protecting group from the 7-sidechain prior to displacement.

The carboxylic acid group of the acylating agent in the first step of this reaction, the 7-acylation, is activated by any of the standard methods known to the art such as conversion to the mixed anhydride, acid chloride, acid imidazolide or activated ester. In addition, a reagent such as dicyclohexylcarbodiimide can be used provided that the carboxyl group on the cephem nucleus is protected with an easily removable protecting group such as a benzhydryl, t-butyl, trichloroethyl, benzyl, benzyloxymethyl, p-methoxybenzyl or p-nitrobenzyl ester. When A is NH$_2$, the α-amino group of the acylating agent is, preferably, protected prior to acylation with an easily removable protective group known in the art such as t-butoxycarbonyl, trichloroethoxycarbonyl, benzyloxycarbonyl, the methyl acetoacetate adduct or similar groups commonly used in the synthesis of peptides.

Alternatively, the compounds of Formula I are prepared by acylation, as described above, of an appropriate 7-amino-3-(carboxyalkyl or carbamoylalkyl substituted oxadiazolylthiomethyl) cephalosporin nucleus of Formula III:

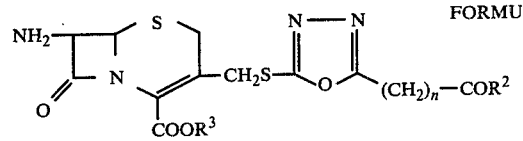
FORMULA III in which:
$n$ is 1 to 5;
R$^2$ is hydroxy, amino, lower alkylamino or di(lower)alkylamino; and
R$^3$ is hydrogen or a protecting ester group, with an appropriate acylating agent followed by removal of the protective groups when present.

The protective groups can be removed according to methods well known to the art, such as with trifluoroacetic acid when t-butyl or t-butoxycarbonyl protective groups are used. The resulting salt is converted to the zwitterionic product or to the free acid by means of a basic ion exchange resin such as polystyreneamine ion exchange resin (Amberlite IR-45) or else by basification of an aqueous solution of the salt.

The acylating agents used as starting materials are either known or prepared by known methods.

The 7-amino-3-(carboxyalkyl and carbamoylalkyl substituted oxadiazolylthiomethyl)cephalosporin starting materials of Formula III are prepared by reaction of 7-aminocephalosporanic acid and a substituted oxadiazole thiol of Formula II and then esterifying.

The carboxyalkyl substituted oxadiazole thiols of Formula II are prepared from reaction of a dithiocarbazic acid salt, prepared from hydrazine and carbon disulfide in the presence of a base such as potassium hydroxide, with a carbalkoxyalkanoic acid halide, preferably chloride, for example ethyl malonyl chloride, followed by thermal cyclization to give a 2-carbalkoxyalkyl-1,3,4-oxadiazole-5-thiol with subsequent hydrolysis of the ester function.

The carbamoylalkyl substituted oxadiazole thiols of Formula II are prepared by treatment of a 2-carbalkoxyalkyl-1,3,4-oxadiazole-5-thiol with ammonia when R$^2$ is amino or with an alkyl- or dialkylamine when R$^2$ is lower alkylamino or di(lower)alkylamino, respectively.

Certain compounds of this invention are capable of forming salts at any acidic or basic groups present with, for example, the alkali metals such as sodium or potassium, the alkaline earth metals such as calcium or with the ammonium cation. When A is NH$_2$, the compounds can exist as the zwitterion or as either an acid or base salt. These salts are prepared by standard methods using a wide variety of non-toxic pharmaceutically acceptable acids and bases known in the art and are also considered as objects of this invention.

It will be recognized that due to the asymmetric α-carbon atom in the 7-acetamido group of Formula I when R$^1$ is

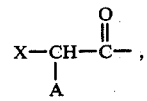

optical isomers will exist. Racemic or resolved products are obtained depending upon whether a racemic or resolved sidechain acid is used as an acylating agent. The resolved sidechain acids are readily obtained from the racemic compounds by resolution according to well known methods, including fractional crystallization of a salt formed with an optically active acid or base. All of the isomers, including separated isomers and mixtures thereof, are included within the scope of this invention.

The compounds of Formula I have exceptional antibacterial activity against both Gram-positive organisms. Minimum inhibitory concentrations (MIC's) range from 0.2 to >200 μg./ml. in in vitro testing. Test results for the compound 7-D-mandelamido-3-(5-carboxymethyl-1,3,4-oxadiazol-2-ylthiomethyl)-3-cephem-4-carboxylic acid and its disodium salt, respectively, are given below:

| Bacteria | MIC (μg./ml.) |
|---|---|
| S. aureus HH 125 | 1.6, 3.1 |
| S. aureus SK 23390 | 0.4, 0.8 |
| S. villaluz SK 70390 | 50, 200 |
| Strep. faecalis HH 34358 | 12.5, 50 |
| E. coli SK 12140 | 0.8, 0.8 |
| E. coli HH 33779 | 1.6, 3.1 |
| Kleb. pneumo. SK 4200 | 0.8, 0.8 |
| Kleb. pneumo. SK 1200 | 0.8, 0.4 |
| Salmonella ATCC 12176 | 0.8, 0.8 |
| Shigella HH 117 | 0.2, 0.4 |
| Pseudo. aerug. HH 63 | >200, >200 |
| Serratia marc. ATCC 13880 | 25, 50 |
| Proteus morgani 179 | 6.3, 6.3 |
| Entero. aerog. ATCC 13048 | 3.1, 3.1 |
| Entero. cloacae HH 31254 | 1.6, 1.6 |

In the in vivo mouse protection test, 7-D-mandelamido-3-(5-carboxymethyl-1,3,4-oxadiazol-2-ylthiomethyl)-3-cephem-4-carboxylic acid exhibited $ED_{50}$'s of 1.56 mg./kg. against E. coli 12140 and 0.86 mg./kg. against Kleb. pneumo. 4200 upon subcutaneous injection.

Pharmaceutical compositions having antibacterial activity which comprise a pharmaceutical carrier containing an active but non-toxic quantity of a compound of Formula I as well as methods of combatting bacterial infections by administering such a composition to an infected host in a non-toxic amount sufficient to combat such infections are also objects of this invention. The administration may be orally or by parenteral injection such as subcutaneously, intramuscularly or intravenously. The injection of suitably prepared sterile solutions or suspensions containing an effective, non-toxic amount of the new cephalosporin compound is the prefered route of administration.

The compounds of Formula I are formulated and administered in the same manner as other cephalosporins. The dosage regimen comprises administration, preferably by injection, of an active but non-toxic quantity of a compound of Formula I selected from the dosage unit range of from 100 to 1000 mg. with the total daily dosage regimen being from 400 mg. to 6 g. The precise dosages are dependent upon the age and weight of the subject and on the infection being treated and can be determined by those skilled in the art based on the data disclosed herein compared with that available to the art attained with known cephalosporins.

The following examples illustrate the invention but are not to be construed as limiting the scope thereof. Temperatures are in degrees Centigrade (° C.) unless otherwise stated.

EXAMPLE 1

7-D-Mandelamido-3-(5-carboxymethyl-1,3,4-oxadiazol-2-ylthiomethyl)-3-cephem-4-carboxylic acid Carbon disulfide (152 g, 2.0 mol) was added dropwise to a cooled (ca. 15°) solution of 130 g (2.0 mol) of potassium hydroxide (85%) and 64 g (2.0 mol) of hydrazine (95%) in 1000 ml of ethanol and the mixture was stirred for 1 hour in the cold. The solid which formed was collected and recrystallized from water-methanol-ethanol to give dithiocarbazic acid potassium salt, m.p. 78°-90° C (dec.).

A solution of 44.4 g (0.296 mol) of ethyl malonyl chloride in 80 ml of tetrahydrofuran and a solution of 29.6 g (0.296 mol) of potassium bicarbonate in 100 ml of water were added simultaneously over a 45 minute interval to a solution of 43.2 g (0.296 mol) of dithiocarbazic acid potassium salt in 200 ml of tetrahydrofuran and 200 ml of water at 5°. The reaction mixture was stirred at 5° for 1 hour then at ambient temperature for 12 hours. The solvents were evaporated and the residue was taken up into 350 ml of ethanol and refluxed on a steam bath for 1.5 hours. The mixture was evaporated to dryness, 300 ml of ethyl acetate and 175 ml of water were added to the residue and it was acidified to pH 2.3 by addition of 3N hydrochloric acid. The layers were separated and the aqueous phase was extracted twice more with 250 ml portions of ethyl acetate. The combined organic extracts were dried (MgSO$_4$), then the solvent was evaporated to give a residue which was dissolved in methylene chloride. The methylene chloride solution was filtered and the filtrate was evaporated to dryness. The residue was chromatographed on silica gel with 98:2:3 chloroform-ethanol-formic acid as eluant to give 2-carbethoxymethyl-1,3,4-oxadiazole-5-thiol as a viscous oil.

$C_6H_8N_2O_3S$ — Calculated: 38.29% C; 4.28% H; 14.88% N. Found: 38.18% C; 4.40% H; 14.61% N.

A solution of 3.15 g (0.017 mol) of 2-carbethoxymethyl-1,3,4-oxadiazole-5-thiol in 25 ml of water and 25 ml of ethanol was stirred for 5 hours while maintaining the pH at 10–11 by addition of 10% aqueous sodium hydroxide solution. The mixture was neutralized to pH 7.0 then evaporated to dryness. The residue was dissolved in 15 ml of water, 50 ml of ethyl acetate was added and the solution was acidified to pH 1.5 with 3N hydrochloric acid. The layers were separated and the aqueous phase was extracted twice with ethyl acetate. The combined extracts were dried (Na$_2$SO$_4$) and the solvent was evaporated to give a residue which was recrystallized from ether-cyclohexane to give 2-carboxymethyl-1,3,4-oxadiazole-5-thiol, m.p. 167°–169° (dec.)

$C_4H_4N_2O_3S$ — Calculated: 29.99% C; 2.52% H; 17.49% N. Found: 30.58% C; 2.90% H; 17.46% N.

A solution of 1.25 g (7.82 mmol) of 2-carboxymethyl-1,3,4-oxadiazole-5-thiol, 3.00 g (7.02 mmol) of 7-D-mandelamidocephalosporanic acid sodium salt and 1.31 g (15.64 mmol) of sodium bicarbonate in 55 ml of water was stirred at 70° for 5.5 hours while maintaining the pH at 7.0 by addition of 5% aqueous sodium bicarbonate. The mixture was chromatographed on XAD-7 resin and eluted with water. The product-containing fractions were lyophilized and the lyophilized material was recrystallized from methanol-ether. The product was taken up in water and lyophilized to give the title compound as the disodium salt.

$C_{20}H_{16}N_4O_8S_2 \cdot 2\,Na \cdot 2\,H_2O \cdot 0.14\,C_4H_{10}O$ — Calculated: 41.98% C; 3.61% H; 9.38% N. Found: 41.70% C; 3.80% H; 8.72% N.

7-D-Mandelamido-3-(5-carboxymethyl-1,3,4-oxadiazol-2-ylthiomethyl)-3-cephem-4-carboxylic acid disodium salt is dissolved in methanol containing a little water and stirred with Amberlite IR-120H ion exchange resin to give the title compound.

EXAMPLE 2

7-(D-α-Aminophenylacetamido)-3-(5-carboxymethyl-1,3,4-oxadiazol-2-ylthiomethyl)-3-cephem-4-carboxylic acid A mixture of 5.22 g (10.0 mmol) of 2-(D-α-t-butoxycarbonylaminophenylacetamido)cephalosporanic acid and 2.40 g (15.0 mmol) of 2-carboxymethyl-1,3,4-oxadiazole-5-thiol in 75 ml of pH 6.4 phosphate buffer solution is treated with sufficient solid sodium bicarbonate to give a pH of 6.4. The mixture is heated at 70° for 4.5 hours, cooled and acifidied to pH 2.5 by addition of 3N hycrochloric acid and extracted with ethyl acetate. The extract is evaporated to dryness and the residue is chromatographed on silica gel to give 7-(D-α-t-butoxycarbonylaminophenylacetamido)-3-(5-carboxymethyl-1,3,4-oxadiazol-2-ylthiomethyl)-3-cephem-4-carboxylic acid.

7-(D-α-t-Butoxycarbonylaminophenylacetamido)-3-(5-carboxymethyl-1,3,4-oxadiazol-2-ylthiomethyl)-3-cephem-4-carboxylic acid is stirred at 25° with 25 ml of trifluoroacetic acid and 25 ml of 1,3-dimethoxybenzene for 1.25 hours. The mixture is evaporated to dryness, ether is added to the residue and the precipitated salt is collected and dissolved in 350 ml of water containing a few drops of trifluoroacetic acid. The aqueous solution is treated with excess Amberlite IR-45 ion-exchange resin to pH 2.7, then lyophilized to give the title compound.

EXAMPLE 3

Reaction of the N-t-butoxycarbonyl derivatives of the following cephalosporanic acids:

7-(α-amino-4-hydroxyphenylacetamido)cephalosporanic acid
7-(α-amino-4-formamidophenylacetamido)cephalosporanic acid
7-(α-amino-3-formamidophenylacetamido)cephalosporanic acid
7-(α-amino-4-ureidophenylacetamido)cephalosporanic acid
7-(α-amino-3-ureidophenylacetamido)cephalosporanic acid
7-(α-amino-4-hydroxymethylphenylacetamido)cephalosporanic acid
7-(α-amino-1,4-cyclohexadienylacetamido)cephalosporanic acid
7-(α-amino-4-carboxymethylaminophenylacetamido)cephalosporanic acid with 2-carboxymethyl-1,3,4-oxadiazole-5-thiol as described in the procedure of Example 2 followed by removal of the protective group and conversion of the trifluoroacetic acid salt to the free acid as described therein gives the following compounds of this invention:

7-(α-amino-4-hydroxyphenylacetamido)-3-(5-carboxymethyl-1,3,4-oxadiazol-2-ylthiomethyl)-3-cephem-4-carboxylic acid
7-(α-amino-4-formamidophenylacetamido)-3-(5-carboxymethyl-1,3,4-oxadiazol-2-ylthiomethyl)-3-cephem-4-carboxylic acid
7-(α-amino-3-formamidophenylacetamido)-3-(5-carboxymethyl-1,3,4-oxadiazol-2-ylthiomethyl)-3-cephem-4-carboxylic acid
7-(α-amino-4-ureidophenylacetamido)-3-(5-carboxymethyl-1,3,4-oxadiazol-2-ylthiomethyl)-3-cephem-4-carboxylic acid
7-(α-amino-3-ureidophenylacetamido)-3-(5-carboxylmethyl-1,3,4-oxadiazol-2-ylthiomethyl)-3-cephem-4-carboxylic acid
7-(α-amino-4-hydroxymethylphenylacetamido)-3-(5-carboxymethyl-1,3,4-oxadiazol-2-ylthiomethyl)-3-cephem-4-carboxylic acid
7-(α-amino-1,4-cyclohexadienylacetamido)-3-(5-carboxymethyl-1,3,4-oxadiazol-2-ylthiomethyl)-3-cephem-4-carboxylic acid
7-(α-amino-4-carboxymethylaminophenylacetamido)-3-(5-carboxymethyl-1,3,4-oxadiazol-2-ylthiomethyl)-3-cephem-4-carboxylic acid.

EXAMPLE 4

7-(4-Hydroxymandelamido)-3-(5-carboxymethyl-1,3,4-oxadiazol-2-ylthiomethyl)-3-cephem-4-carboxylic acid is prepared by reaction of 7-(4-hydroxymandelamido)cephalosporanic acid sodium salt, 2-carboxymethyl-1,3,4-oxadiazole-5-thiol and sodium bicarbonate as described in the procedure of Example 1 followed by conversion of the product salt to the free acid as described therein.

EXAMPLE 5

When the sodium salt of a cephalosporanic acid listed below:

7-(3-sydnoneacetamido)cephalosporanic acid
7-(2-thienylacetamido)cephalosporanic acid
7-(1-tetrazolylacetamido)cephalosporanic acid is reacted with 2-carboxymethyl-1,3,4-oxadiazole-5-thiol and sodium bicarbonate by the procedure described in Example 1 and the product is converted to the free acid as described therein, the following compounds of this invention are obtained, respectively:

7-(3-sydnoneacetamido)-3-(5-carboxymethyl-1,3,4-oxadiazol-2-ylthiomethyl)-3-cephem-4-carboxylic acid
7-(2-thienylacetamido)-3-(5-carboxymethyl-1,3,4-oxadiazol-2-ylthiomethyl)-3-cephem-4-carboxylic acid
7-(1-tetrazolylacetamido)-3-(5-carboxymethyl-1,3,4-oxadiazol-2-ylthiomethyl)-3-cephem-4-carboxylic acid.

EXAMPLE 6

7-(2-Aminomethylphenylcetamido)-3-(5-carboxymethyl-1,3,4-oxadiazol-2-ylthiomethyl)-3-cephem-4-carboxylic acid When 7-(2-aminomethylphenylacetamido)cephalosporanic acid sodium salt is reacted with 2-carboxymethyl-1,3,4-oxadiazole-5-thiol and sodium bicarbonate by the procedure described in Example 1 and the product is converted to the free acid as described therein, the title compound is obtained.

EXAMPLE 7

7-Trifluoromethylthioacetamido-3-(5-carboxymethyl-1,3,4-oxadiazol-2-ylthiomethyl)-3-cephem-4-carboxylic acid To an aqueous solution of 1.95 g (12.2 mmol) of 2-carboxymethyl-1,3,4-oxadiazole-5-thiol and 2.05 g (24.4 mmol) of sodium bicarbonate in 35 ml of water is added 3.42 g (8.1 mmol) of 7-trifluoromethylthioacetamidocephalosporanic acid sodium salt. The reaction mixture is stirred at 70° for 4.5 hours, then cooled and chromatographed on XAD-2 resin with water and methanol as eluants. The product-containing fractions are combined and evaporated to dryness to give a residue which is stirred with 30 ml of water. Ethyl acetate is added and the resulting mixture is filtered. The layers are separated and the aqueous phase is lyophilized to give 7-trifluoromethylthioacetamido-3-(5-carboxymethyl-1,3,4-oxadiazol-2-ylthiomethyl)-3-cephem-4-carboxylic acid disodium salt.

7-Trifluoromethylthioacetamido-3-(5-carboxymethyl-1,3,4-oxadiazol-2-ylthiomethyl)-3-cephem-4-carboxylic acid disodium salt is dissolved in a minimum amount of water to which ethyl acetate is added. While stirring, 3N hydrochloric acid is added until the solution is acidified to pH 2.5. The layers are separated, the aqueous phase is extracted with ethyl acetate and the combined extracts are washed with water, dried (MgSO$_4$) and evaporated to dryness to give the title compound.

EXAMPLE 8

Reaction of the sodium salt of a cephalosporanic acid listed below:

7-(2,2,2-trifluoroethylthioacetamido)cephalosporanic acid
7-trifluoromethylsulfinylacetamidocephalosporanic acid with 2-carboxymethyl-1,3,4-oxadiazole-5-thiol and sodium bicarbonate as described in the procedure of Example 7 gives, after conversion of the product salts to the free acids as described therein, the following compounds of this invention as final products:

7-(2,2,2-trifluoroethylthioacetamido)-3-(5-carboxymethyl-1,3,4-oxadiazol-2-ylthiomethyl)-3-cephem-4-carboxylic acid
7-trifluoromethylsulfinylacetamido-3-(5-carboxymethyl-1,3,4-oxadiazol-2-ylthiomethyl-3-cephem-4-carboxylic acid.

EXAMPLE 9

7-Amino-3-(5-carboxymethyl-1,3,4-oxadiazol-2-ylthiomethyl)-3-cephem-4-carboxylic acid A solution of 9.61 g (0.06 mol) of 2-carboxymethyl-1,3,4-oxadiazole-5-thiol in 120 ml of acetone is added to a warm (45°) solution of 10.9 g (0.04 mol) of 7-aminocephalosporanic acid in a mixture of 220 ml of water, 50 ml of acetone and 13.44 g (0.16 mol) of sodium bicarbonate. The temperature is raised to 65° and the pH maintained at 7.4–7.6 by addition of aqueous sodium carbonate solution. After 3 hours, the acetone is removed in vacuo and the reaction mixture is cooled to 10° and adjusted a pH 3.5 by addition of dilute hydrochloric acid. The product is collected, washed with water and then acetone to give the title compound.

EXAMPLE 10

When an equivalent amount of an acid chloride prepared from the following acid esters:

succinic acid monomethyl ester
glutaric acid monomethyl ester adipic acid monoethyl ester
pimelic acid monomethyl ester
by treatment with thionyl chloride or phosphorus pentachloride is used in the procedure of Example 1 in place of ethyl malonyl chloride in the reaction with dithiocarbazic acid potassium salt and the resulting ester substituted oxadiazole compounds are hydrolyzed as described therein, the following acid substituted oxadiazole thiols are prepared:

2-(2-carboxyethyl)-1,3,4-oxadiazole-5-thiol
2-(3-carboxypropyl)-1,3,4-oxadiazole-5-thiol

EXAMPLE 11

7-(2,2,2-Trifluoroethylsulfinylacetamido)-3-(5-carboxymethyl-1,3,4-oxadiazol-2-ylthiomethyl)-3-cephem-4-carboxylic acid 2-(4-carboxybutyl)-1,3,4-oxadiazole-5-thiol
2-(5-carboxypentyl)-1,3,4-oxadiazole-5-thiol.

Reaction of a 2-carboxyalkyl-1,3,4-oxadiazole-5-thick listed above with 7-D-mandelamidocephalosporanic acid sodium salt and sodium bicarbonate according to the procedure described in Example 1 followed by conversion of the salts formed to the free acids gives the following compounds of this invention:

7-D-mandelamido-3-[5-(2-carboxyethyl)-1,3,4-oxadiazol-2-ylthiomethyl]-3-cephem-4-carboxylic acid
7-D-mandelamido-3-[5-(3-carboxypropyl)-1,3,4-oxadiazol-2-ylthiomethyl]-3-cephem-4-carboxylic acid
7-D-mandelamido-3-[5-(4-carboxybutyl)-1,3,4-oxadiazol-2-ylthiomethyl]-3-cephem-4-carboxylic acid
7-D-mandelamido-3-[5-(5-carboxypentyl)-1,3,4-oxadiazol-2-ylthiomethyl]-3-cephem-4-carboxylic acid.

Likewise, reaction of the substituted oxadiazole thiols listed above with any of the 7-acyl cephalosporanic acids mentioned herein or their corresponding salts according to procedures described herein gives the corresponding compounds of this invention.

To a stirred solution of 5.7 g (0.03 mol) of 2,2,2-trifluoroethylsulfinylacetic acid and 3.45 g (0.03 mol) of N-hydroxysuccinimide in 50 ml of tetrahydrofuran at 0° is added 6.2 g (0.031 mol) of dicyclohexylcarbodiimide. The reaction mixture is stirred at 0° for 1 hour then at 25° for 12 hours. The precipitate is filtered and washed with tetrahydrofuran and the filtrate is evaporated to dryness to give the activated ester of 2,2,2-trifluoroethylsulfinylacetic acid.

A suspension of 3.4 g (0.01 mol) of 7-amino-3-(5-carboxymethyl-1,3,4-oxadiazol-2-ylthiomethyl)-3-cephem-4-carboxylic acid in 50 ml of dry dimethylformamide is treated with 2 ml of triethylamine and the mixture is stirred for 15 minutes at 25°. A slight excess of 0.01 mol of the activated ester of 2,2,2-trifluoroethylsulfinylacetic acid is added to the mixture and it is stirred an additional hour. The reaction mixture is evaporated to dryness in vacuo and water and ethyl acetate are added to the residue. The layers are separated, the ethyl acetate layer is discarded, fresh ethyl acetate is added to the aqueous phase and it is acidified to pH 2.5 by addition of 6N hydrochloric acid. The mixture is filtered, the layers are separated and the aqueous phase is extracted with ethyl acetate. The combined extracts are washed with water, dried (MgSO$_4$) and evaporated to dryness to give the title compound.

EXAMPLE 12

7-Methylthioacetamido-3-(5-carboxymethyl-1,3,4-oxadiazol-2-ylthiomethyl)-3-cephem-4-carboxylic acid To a stirred, cooled (−20°) solution of 8.8 g (0.026 mol) of 7-amino-3-(5-carboxymethyl-1,3,4-oxadiazol-2-ylthiomethyl)3-cephem-4-carboxylic acid in 220 ml of 3% sodium bicarbonate and 220 ml of acetone is added dropwise a solution of 3.66 g (0.029 mol) of methylthioacetyl chloride in 52 ml of acetone, during which time the pH of the reaction mixture is maintained at 8.0 by addition of 10% sodium hydroxide. After addition the reaction mixture is stirred an additional 20 minutes at −15°, then is warmed to 25° and extracted with ether. The remaining aqueous phase is cooled, 250 ml of ethyl acetate is added and the slurry is acidified with 3n hydrochloric acid. The layers are separated and the aqueous phase is extracted twice more with ethyl acetate. The combined extracts are dried ($MgSO_4$) and evaporated to dryness to yield the title compound.

EXAMPLE 13

7-(D-α-Formyloxyphenylacetamido)-3-(5-carboxymethyl-1,3,4-oxadiazol-2-ylthiomethyl)-3-cephem-4-carboxylic acid A mixture of 3.4 g (0.01 mol) of 7-amino-3-(5-carboxymethyl-1,3,4-oxadiazol-2-ylthiomethyl)-3-cephem-4-carboxylic acid, 3.97 g (0.02 mol) of the formate ester of D-mandeloyl chloride and 3.36 g (0.4 mol) of sodium bicarbonate in 100 ml of water and 140 ml of acetone is stirred in the cold for 1 hour, then at 25° for 2 hours. The acetone is evaporated in vacuo and the remaining aqueous mixture is extracted with ethyl acetate. The aqueous solution is added with stirring to a cold mixture of 100 ml of water and 200 ml of ethyl acetate and the pH of the resulting mixture is adjusted to 2.0 by addition of 6N hydrochloric acid. The mixture is filtered, the layers are separated and the ethyl acetate layer is washed with water, dried ($MgSO_4$) and evaporated to dryness to give the title compound.

EXAMPLE 14

Acylation of 7-amino-3-(5-carboxymethyl-1,3,4-oxadiazol-2-ylthiomethyl)-3-cephem-4-carboxylic acid with an activated derivative of an acid listed below:

cyanoacetic acid
cyanomethylthioacetic acid
3-pyridylthioacetic acid
4-pyridylthioacetic acid
2-pyridone-N-acetic acid
4-pyridone-N-acetic acid as described in the procedure of Example 11 gives the following compounds of this invention:
7-cyanoacetamido-3-(5-carboxymethyl-1,3,4-oxadiazol-2-ylthiomethyl)-3-cephem-4-carboxylic acid
7-cyanomethylthioacetamido-3-(5-carboxymethyl-1,3,4-oxadiazol-2-ylthiomethyl)-3-cephem-4-carboxylic acid
7-(3-pyridylthioacetamido)-3-(5-carboxymethyl-1,3,4-oxadiazol-2-ylthiomethyl)-3-cephem-4-carboxylic acid
7-(4-pyridylthioacetamido)-3-(5-carboxymethyl-1,3,4-oxadiazol-2-ylthiomethyl)-3-cephem-4-carboxylic acid
7-(2-pyridoneacetamido)-3-(5-carboxymethyl-1,3,4-oxadiazol-2-ylthiomethyl)-3-cephem-4-carboxylic acid
7-(4-pyridoneacetamido)-3-(5-carboxymethyl-1,3,4-oxadiazol-2-ylthiomethyl)-3-cephem-4-carboxylic acid.

EXAMPLE 15

Reaction of a cephalosporanic acid listed below or its corresponding salt:

7-(α-hydroxy-2-thienylacetamido)cephalosporanic acid
7-(α-carboxy-2-thienylacetamido)cephalosporanic acid
7-(α-sulfophenylacetamido)cephalosporanic acid with 2-carboxymethyl-1,3,4-oxadiazol-5-thiol in the presence of sodium bicarbonate by procedures described hereinabove gives, after conversion of the products to the free acids, the following compounds of this invention:

7-(α-hydroxy-2-thienylacetamido)-3-(5-carboxymethyl-1,3,4-oxadiazol-2-ylthiomethyl)-3-cephem-4-carboxylic acid
7-(α-carboxy-2-thienylacetamido)-3-(5-carboxymethyl-1,3,4-oxadiazol-2-ylthiomethyl)-3-cephem-4-carboxylic acid
7-(α-sulfophenylacetamido)-3-(5-carboxymethyl-1,3,4-oxadiazol-2-ylthiomethyl)-3-cephem-4-carboxylic acid.

EXAMPLE 16

7-(2,2,2-Trifluoroethylsulfonylacetamido)-3-(5-carboxymethyl-1,3,4-oxadiazol-2-ylthiomethyl)-3-cephem-4-carboxylic acid To a suspension of 1.86 g (5 mmol) of 7-amino-3-(5-carboxymethyl-1,3,4-oxadiazol-2-ylthiomethyl)-3-cephem-4-carboxylic acid in 50 ml of methylene chloride is dropwise added over a 30 minute period 6.0 g (0.03 mol) of O-t-butyl-N,N′-diisopropylpseudourea in 10 ml of methylene chloride. The reaction mixture is stirred at ambient temperature for 78 hours then filtered. The filtrate is concentrated and 200 ml of benzene is added to the residue. The benzene solution is filtered and the filtrate is stirred with 1N hydrochloric acid in an ice bath for 30 minutes. The layers are separated and the organic phase is again treated with hydrochloric acid. The acidic aqueous phases are combined, adjusted to pH 7.5 by addition of solid sodium bicarbonate and extracted with ethyl acetate. The extract is dried ($MgSO_4$), filtered and evaporated to dryness to give 7-amino-3-(5-carboxymethyl-1,3,4-oxadiazol-2-ylthiomethyl)-3-cephem-4-carboxylic acid di-t-butyl ester.

To a solution of 5.24 g (0.019 mol) of 7-amino-3-(5-carboxymethyl-1,3,4-oxadiazol-2-ylthiomethyl)-3-cephem-4-carboxylic acid di-t-butyl ester and 3.9 g (0.019 mol) of 2,2,2-trifluoroethylsulfonylacetic acid in tetrahydrofuran is added dropwise a solution of 3.9 g (0.019 mol) of dicyclohexylcarbodiimide in 100 ml of tetrahydrofuran. The reaction mixture is stirred at 25° for 12 hours, then filtered and concentrated to about 10 ml. The residue is filtered and evaporated to dryness to give 7-(2,2,2-trifluoroethylsulfonylacetamido)-3-(5-carboxymethyl-1,3,4-oxadiazol-2-ylthiomethyl)-3-cephem-4-carboxylic acid di-t-butyl ester.

The diester is dissolved in acetonitrile and trifluoroacetic acid is added. The solution is stirred for 3 hours and then added to rapidly stirring ether to precipitate the title compound.

EXAMPLE 17

7-D-Mandelamido-3-(5-carbamoylmethyl-1,3,4ox-adiazol-2-ylthiomethyl)-3-cephem-4-carboxylic acid A solution of 1.88 g (0.01 mol) of 2-carbethoxymethyl-1,3,4-oxadiazol-5-thiol in 25 ml of absolute ethanol is added dropwise at ambient temperature to 100 ml of a saturated solution of anhydrous ammonia in absolute ethanol. When the reaction is complete, as evidenced by thin layer chromatography, the solution is evaporated to dryness. The residue is dissolved in 100 ml of water and the aqueous solution is acidified to pH 2.5 with dilute hydrochloric acid and extracted with ethyl acetate. The extract is dried ($MgSO_4$) and evaporated to dryness to give 2-carbamoylmethyl-1,3,4-oxadiazole-5-thiol.

2-Carbamoylmethyl-1,3,4-oxadiazole-5-thiol (12.4 g, 7.8 mmol), 3.00 (7.02 mmol) of 7-D-mandelamidocephalosporanic acid sodium salt and 0.66 g (7.82 mmol) of sodium bicarbonate are reacted as described in the procedure of Example 1. After cooling, the reaction mixture is acidified to pH 2.0 and extracted with ethyl acetate. The extracts are combined and dried and the solvent is evaporated to give the title compound.

EXAMPLE 18

7-D-Mandelamido-3-[5-(N-methylcarbamoylmethyl)-1,3,4-oxadiazol-2-ylthiomethyl]-3-cephem-4-carboxylic acid Reaction of 2-carbethoxymethyl-1,3,4-oxadiazole-5-thiol and methylamine according to the procedure of Example 17 gives 2-(N-methylcarbamoylmethyl)-1,3,4-oxaidazole-5-thiol.

2-(N-Methylcarbamoylmethyl)-1,3,4-oxadiazole-5-thiol, 7-D-mandelamidocephalosporanic acid sodium salt and sodium bicarbonate are reacted as described in the procedure of Example 17.

After cooling, the reaction mixture is acidified and extracted with ethyl acetate. The extract is dried and evaporated to dryness to give the title compound.

EXAMPLE 19

7-D-Mandelamido-3-[5-(N,N-dimethylcarbamoylmethyl)-1,3,4-oxadiazol-2-ylthiomethyl]-3-cephem-4-carboxylic acid Substitution of dimethylamine in the procedure of Example 17 in place of ammonia in the reaction with 2-carbethoxymethyl-1,3,4-oxadiazole-5-thiol gives 2-(N,N-dimethylcarbamoylmethyl)-1,3,4-oxadiazole-5-thiol.

2-(N,N-Dimethylcarbamoylmethyl)-1,3,4-oxadiazole-5-thiol, 7-D-mandelamidocephalosporanic acid sodium salt and sodium bicarbonate are reacted as described in the procedure of Example 17. After cooling, the reaction mixture is acidified and extracted with ethyl acetate. The extract is dried and evaporated to dryness to give the title compound.

EXAMPLE 20

Reaction of the ethyl ester of an acid substituted 1,3,4-oxadiazole-5-thiol listed in Example 10 with ammonia as described in the procedure of Example 17 gives, after acidification, the following carbamoylalkyl substituted 1,3,4-oxadiazole thiols:

2-(2-carbamoylethyl)-1,3,4-oxadiazole-5-thiol
2-(3-carbamoylpropyl)-1,3,4-oxadiazole-5-thiol
2-(4-carbamoylbutyl)-1,3,4-oxadiazole-5-thiol
2-(5-carbamoylpentyl)-1,3,4-oxadiazole-5-thiol.

Substitution of a carbamoylalkyl substituted oxadiazole thiol listed above in the procedue described in Example 17 in place of 2-carbamoylmethyl-1,3,4-oxadiazole-5-thiol gives the cephalosporin compounds of this invention listed below as final products:

7-D-mandelamido-3-[5-(2-carbamoylethyl)-1,3,4-oxadiazol-2-ylthiomethyl]-3-cephem-4-carboxylic acid
7-D-mandelamido-3-[5-(3-carbamoylpropyl)-1,3,4-oxadiazol-2-ylthiomethyl]-3-cephem-4-carboxylic acid
7-D-mandelamido-3-[5-(4-carbamoylbutyl)-1,3,4-oxadiazol-2-ylthiomethyl]-3-cephem-4-carboxylic acid
7-D-mandelamido-3-[5-(5-carbamoylpentyl)-1,3,4-oxadiazol-2-ylthiomethyl]-3-cephem-4-carboxylic acid.

In a similar manner, other 7-acyl-3-(5-carbamoylalkyl-1,3,4-oxadiazol-2-ylthiomethyl)-3-cephem-4-carboxylic acids of this invention are prepared by substitution of a 2-carbamoylalkyl-1,3,4-oxadiazole-5-thiol in the appropriate procedure described hereinabove.

EXAMPLE 21

When ethylamine, propylamine or butylamine is reacted with 2-carbethoxymethyl-1,3,4-oxadiazole-5-thiol according to the procedure of Example 17, the following N-alkylcarbamoylalkyl substituted oxadiazole thiols are ultimately prepared:

2-(N-ethylcarbamoylmethyl)-1,3,4-oxadiazole-5-thiol
2-(N-propylcarbamoylmethyl)-1,3,4-oxadiazole-5-thiol
2-(N-butylcarbamoylmethyl)-1,3,4-oxadiazole-5-thiol.

Reaction of a substituted oxadiazole thiol listed above with 7-D-mandelamidocephalosporanic acid sodium salt and sodium bicarbonate according to the procedure described in Example 17 gives the following compounds of this invention as final products:

7D-mandelamido-3-[5-(N-ethylcarbamoylmethyl)-1,3,4-oxadiazol-2-ylthiomethyl]-3-cephem-4-carboxylic acid
7-Di-mandelamido-3-[5-(N-propylcarbamoylmethyl)-1,3,4-oxadiazol-2-ylthiomethyl]-3-cephem-4-carboxylic acid
7-D-mandelamido-3-[5-(N-butylcarbamoylmethyl)-1,3,4-oxadiazol-2-ylthiomethyl]-3-cephem-4-carboxylic acid.

Similarly, the alkylcarbamoylalkyl substituted oxadiazole thiols listed above are substituted in the appropriate procedures described hereinabove to produce other 7-acyl cephalosporin compounds of this invention.

EXAMPLE 22

When diethylamine, dipropylamine or dibutylamine is substituted for ammonia in the procedure of Example 17, the following oxadiazole thiols are ultimately prepared:

2-(N,N-diethylcarbamoylmethyl)-1,3,4-oxadiazole-5-thiol 2-(N,N-dipropylcarbamoylmethyl)-1,3,4-oxadiazole-5-thiol 2-(N,N-dibutylcarbamoylmethyl)-1,3,4-oxadiazole-5-thiol.

Reaction of a substituted oxadiazole thiol listed above with 7-D-mandelamidocephalosporanic acid sodium salt and sodium bicarbonate according to the procedure described in Example 17 gives the following compounds of this invention as final products:

7-D-mandelamido-3-[5-(N,N-diethylcarbamoylmethyl)-1,3,4-cxadiazol-2-ylthiomethyl]-3-cephem-4-carboxylic acid 7-D-mandelamido-3-[5-(N,N-dipropylcarbamoylmethyl)-1,3,4-oxadiazol-2-ylthiomethyl]-3-cephem-4-carboxylic acid 7-D-mandelamido-3-[5-(N,N-dibutylcarbamoylmethyl)-1,3,4-oxadiazol-2-ylthiomethyl]-3-cephem-4-carboxylic acid.

By similar procedures, the other 7-acyl-3-[5-(N,N-dialkylcarbamoylmethyl)-1,3,4-oxadiazol-2-ylthiomethyl] cephalosporin compounds of this invention are prepared by substitution of the dialkylcarbamoylmethyl substituted oxadiazole thiols listed above in the appropriate procedures described hereinabove.

EXAMPLE 23

An injectable pharmaceutical composition is formed by adding sterile water or sterile saline solution (2 ml) to 500 mg of 7-D-mandelamido-3-(5-carboxymethyl-1,3,4-oxadiazol-2-ylthiomethyl)-3-cephem-4-carboxylic acid disodium salt. A unit dose is administered intramuscularly to a subject infected with an organism susceptible to the compound as noted herebefore every 4 to 6 hours. Intravenous or drip administration is also similarly used.

Pharmaceutrial compositions of the other antibacterial compounds disclosed above may be formulated and used in a similar manner.

What is claimed is:

1. A compound of the formula:

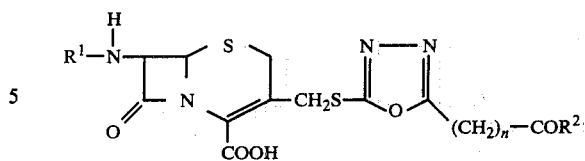

in which:

$R^1$ is an acyl group of the formula:

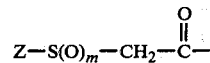

where:

Z is methyl, trifluoromethyl, trifluoroethyl, pyridyl or cyanomethyl;

$m$ is zero to two;

$n$ is one to five; and $R^2$ is hydroxy, amino, lower alkylamino or di(lower)alkylamino, or non-toxic pharmaceutically acceptable salt thereof.

2. A compound according to claim 1 in which $n$ is 1.

3. A compound according to claim 1 in which Z is trifluoromethyl or cyanomethyl.

4. A compound according to claim 3, said compound being 7-cyanomethylthioacetamido-3-(5-carboxymethyl-1,3,4-oxadiazol-2-ylthiomethyl)-3-cephem-4-carboxylic acid.

5. A compound according to claim 3, said compound being 7-trifluoromethylthioacetamido-3-(5-carboxymethyl-1,3,4-oxadiazol-2-ylthiomethyl)-3-cephem-4-carboxylic acid.

6. A pharmaceutical composition having antibacterial activity comprising a nontoxic, antibacterial quantity of a compound as claimed in claim 1 and a pharmaceutically acceptable carrier therefor.

7. A method of treating bacterial infections comprising administering internally by injection to an infected or susceptible warm-blooded animal an antibacterially effective but nontoxic dose of a compound as claimed in claim 1.

8. A pharmaceutical composition having antibacterial activity comprising a nontoxic, antibacterial quantity of a compound as claimed in claim 4 and a pharmaceutically acceptable carrier therefor.

9. A pharmaceutical composition having antibacterial activity comprising a nontoxic, antibacterial quantity of a compound as claimed in claim 5 and a pharmaceutically acceptable carrier therefor.

10. A method as claimed in claim 7 in which the compound is 7-cyanomethylthioacetamido-3-(5-carboxymethyl-1,3,4-oxadiazol-2-ylthiomethyl)-3-cephem-4-carboxylic acid.

11. A method as claimed in claim 7 in which the compound is 7-trifluoromethylthioacetamido-3-(5-carboxymethyl-1,3,4-oxadiazol-2-ylthiomethyl)-3-cephem-4-carboxylic acid.

* * * * *